United States Patent
Ezoe et al.

(10) Patent No.: US 9,314,171 B2
(45) Date of Patent: *Apr. 19, 2016

(54) BLOOD PRESSURE MEASUREMENT DEVICE HAVING FUNCTION OF DETERMINING REST CONDITION OF PATIENT

(71) Applicant: OMRON HEALTHCARE Co., Ltd., Kyoto (JP)

(72) Inventors: Mika Ezoe, Osaka (JP); Yukiya Sawanoi, Nara (JP); Shingo Yamashita, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 181 days.

This patent is subject to a terminal disclaimer.

(21) Appl. No.: 13/955,314

(22) Filed: Jul. 31, 2013

(65) Prior Publication Data

US 2015/0038801 A1 Feb. 5, 2015

(51) Int. Cl.
*A61B 5/09* (2006.01)
*A61B 5/024* (2006.01)
*A61B 5/022* (2006.01)
*A61B 5/00* (2006.01)

(52) U.S. Cl.
CPC .............. *A61B 5/022* (2013.01); *A61B 5/02405* (2013.01); *A61B 5/742* (2013.01)

(58) Field of Classification Search
CPC ........ A61B 5/022; A61B 5/024; A61B 5/742; A61B 5/7282; A61B 18/22; A61B 18/2277; G02B 6/262; G02B 6/0283; G02B 6/03627
USPC ......... 600/300, 301, 481, 483–485, 495, 500, 600/501, 509, 513
See application file for complete search history.

(56) References Cited

U.S. PATENT DOCUMENTS

| | | | | |
|---|---|---|---|---|
| 5,475,725 A | * | 12/1995 | Nakamura | 377/24.2 |
| 6,447,457 B1 | * | 9/2002 | Forstner et al. | 600/485 |
| 6,929,610 B2 | * | 8/2005 | Forstner | 600/485 |
| 2001/0049476 A1 | * | 12/2001 | Forstner | 600/494 |
| 2004/0097815 A1 | * | 5/2004 | Forstner | 600/485 |
| 2005/0187480 A1 | * | 8/2005 | Kario et al. | 600/483 |
| 2011/0237963 A1 | * | 9/2011 | Nishioka et al. | 600/493 |

FOREIGN PATENT DOCUMENTS

JP 2012-120206 A 6/2012

* cited by examiner

*Primary Examiner* — Gary Jackson
*Assistant Examiner* — Boniface N Nganga
(74) *Attorney, Agent, or Firm* — Osha Liang LLP

(57) ABSTRACT

A blood pressure measurement device measures a pulse period of a patient and includes a memory, a threshold calculation section, a rest/unrest condition determination section, and a display unit. The memory stores data of the measured pulse period and data of a pulse period of past measurement of the patient. The threshold calculation section calculates a threshold value range based on the data of the pulse period of the past measurement of the patient. The rest/unrest condition determination section determines whether the patient was under the rest condition or the unrest condition during blood pressure measurement by comparing the measured pulse period with the threshold value range. The display unit displays the blood pressure measured and whether the blood pressure was measured when the patient was in the rest condition or the unrest condition.

11 Claims, 5 Drawing Sheets

FIG. 3A

Patient A

| | | Systolic | Diastolic | Pulse Rate | Pulse Period Change (sec) | Time Zone |
|---|---|---|---|---|---|---|
| | 1) | 120 | 83 | 81 | 0.032 | Daytime |
| | 2) | 127 | 87 | 86 | 0.032 | Daytime |
| | 3) | 126 | 87 | 76 | 0.036 | Daytime |
| 1,2,3 Ave | | 124 | 86 | 81 | 0.033 | |
| | 4) | 161 | 97 | 101 | 0.104 | Daytime |

FIG. 3B

Patient B

| | | Systolic | Diastolic | Pulse Rate | Pulse Period Change (sec) | Time Zone |
|---|---|---|---|---|---|---|
| | 5) | 129 | 87 | 88 | 0.032 | Daytime |
| | 6) | 127 | 88 | 88 | 0.030 | Daytime |
| | 7) | 126 | 87 | 88 | 0.048 | Night Time |
| 5,6,7 Ave | | 127 | 87 | 88 | 0.037 | |
| | 8) | 134 | 92 | 98 | 0.084 | Daytime |

Patient: A

Systolic Pressure: 161

Diastolic Pressure: 97

Pulse Period Change: 0.104 sec

Condition: Unrest

*FIG. 5A*

Patient: B

Systolic Pressure: 134 mm Hg

Diastolic Pressure: 92 mm Hg

Pulse Rate: 98

Condition: Rest

*FIG. 5B*

BLOOD PRESSURE MEASUREMENT DEVICE HAVING FUNCTION OF DETERMINING REST CONDITION OF PATIENT

BACKGROUND (1) Field of the Invention

The present invention relates to a blood pressure measurement device and methods for measuring blood pressure. More specifically, the present invention relates to apparatus and methods for determining whether a patient was in a rest condition during blood pressure measurement.

(2) Description of Related Art

A rest condition of a patient is important when measuring blood pressure. If the patient is not in a rest condition, the measured blood pressure may differ from the value measured in the rest condition. Thus, it is necessary to know whether the patient was in the rest condition when the blood pressure was being measured.

As a measure to determine whether a patient was in a rest condition, measuring pulse rate and pulse wave period is known. Generally, the patient's pulse wave period becomes short or unstable after hard exercise or mental distress. Therefore, it is possible to determine whether the patient was in the rest condition by examining whether the patient's pulse wave period was stable during a certain period of time.

Rossmax Hemodynamic Stability Determination (HSD) determines a rest condition of a patient by measuring the patient's pulse period. However, because each individual has a significantly different pulse period in connection with both pulse rate and pulse period change, it is difficult to determine whether the patient was in a rest condition or an unrest condition at the time of measurement of blood pressure by comparing the measured pulse period with a general or standard value of the pulse period.

JPH2012-120206 discloses a relationship between the pulse rate and the pulse period change. As shown in FIG. 9 of JPH2012-120206, when a patient receives a stress, the pulse rate and the pulse period change of a patient are influenced differently by the stress. Therefore, it is possible that when the pulse period change of the patient is significantly increased over a certain period of time by receiving a stress, the pulse rate over the same period of time remains unchanged. Therefore, when the pulse period is measured in order to determine the rest/unrest condition of the patient, examining the pulse period change (variability) in addition to the pulse rate is useful and desirous.

In addition, the pulse wave period of a patient is significantly influenced by the time zone (time of day), day of the week, season, environmental temperature, etc. Thus, these conditions at the time of measurement should also be taken into account.

Because prior art blood pressure measurement devices do not adequately consider that the rest or unrest condition significantly differs from patient to patient, these devices may provide inaccurate blood pressure value measurements.

SUMMARY OF INVENTION

According to one or more embodiments of the present invention, the pulse period of the patient is measured and compared with a pulse period of the same patient obtained in his/her past measurement(s) and stored in a memory of a blood pressure measurement device.

According to one or more embodiments of the present invention, the comparison of the "pulse period" may be made in connection with: a time period between pulse waves (pulse rate) or a change of time period between the pulse waves (pulse rate variability), or both.

According to one or more embodiments of the present invention, if the measured pulse period is different from the pulse period of past measurement by more than a threshold value, the patient is determined to have been in an unrest condition at the time of measurement.

According to one or more embodiments of the present invention, the threshold value, which is used to determine the rest/unrest condition of the patient, may be calculated based on the data of the pulse period of the patient in his/her past measurement.

According to one or more embodiments of the present invention, in setting the threshold value, a condition at the time of measurement, such as the time zone (time of day), day of the week, season, or environmental temperature may be taken into account.

In accordance with one or more embodiments of the present invention, a blood pressure measurement device determines whether a patient was in a rest condition or an unrest condition during blood pressure measurement, and the device includes means for measuring a pulse period of the patient; a memory that stores data of the measured pulse period and data of a pulse period of a past measurement of the patient; a threshold calculation section that calculates a threshold value range based on the data of the pulse period of the past measurement of the patient; a rest/unrest condition determination section that determines whether the patient was in the rest condition or the unrest condition during blood pressure measurement by comparing the measured pulse period with the threshold value range based on the data of the pulse period of the past measurement of the patient; and a display unit that displays the blood pressure measured and whether the blood pressure was measured when the patient was in the rest condition or the unrest condition.

In accordance with one or more embodiments of the present invention, a blood pressure measurement device determines whether a patient was in a rest condition or an unrest condition during blood pressure measurement, and the device includes a cuff having an air bladder, wherein the cuff is configured to be wrapped around a measurement site of the patient; a measurement air system including a pressure sensor, a pump, and a valve; an air tube that connects the air bladder of the cuff to the measurement air system; a blood pressure calculation section that calculates a blood pressure of the patient based on an internal pressure of the air bladder as detected by the pressure sensor; a pulse rate/pulse period change calculation section that calculates a pulse rate and a pulse period change of the patient based on a measured pulse period of the patient; a memory that stores the pulse rate and the pulse period change of the patient and data of a pulse period of a past measurement of the patient; a threshold calculation section that calculates a threshold value range based on the data of the pulse period of the past measurement of the patient; a rest/unrest condition determination section that determines whether the patient was in the rest condition or the unrest condition during blood pressure measurement by comparing the pulse rate or the pulse period change of the patient with the threshold value range based on the data of the pulse period of the past measurement of the patient; and a display unit that displays the blood pressure measured and whether the blood pressure was measured when the patient was in the rest condition or the unrest condition.

According to one or more embodiments of the present invention, a method of determining whether a patient was in a rest condition or an unrest condition during blood pressure measurement includes measuring a blood pressure, a pulse rate, and a pulse period change of the patient; storing data of the pulse rate and the pulse period change obtained by the measurement in a memory; calculating a threshold value range based on data of a pulse rate and a pulse period change of a past measurement of the patient; determining whether the patient was in the rest condition or the unrest condition during blood pressure measurement by comparing the measured pulse rate and the measured pulse period change with the threshold value range based on data of the pulse rate and the pulse period change of the past measurement of the patient; and displaying on a display unit the blood pressure measured and whether the blood pressure was measured when the patient was in the rest condition or the unrest condition.

BRIEF DESCRIPTION OF DRAWINGS

FIGS. 3A and 3B are examples of data tables that show the blood pressure measurements, pulse rates, pulse period changes, and time zones (times of day) of Patient A and Patient B according to one or more embodiments of the present invention.

FIGS. 5(A) and 5(B) are example displays of the data shown in FIGS. 3(A) and 3(B) according to one or more embodiments of the present invention.

DETAILED DESCRIPTION OF INVENTION

Figure 1:
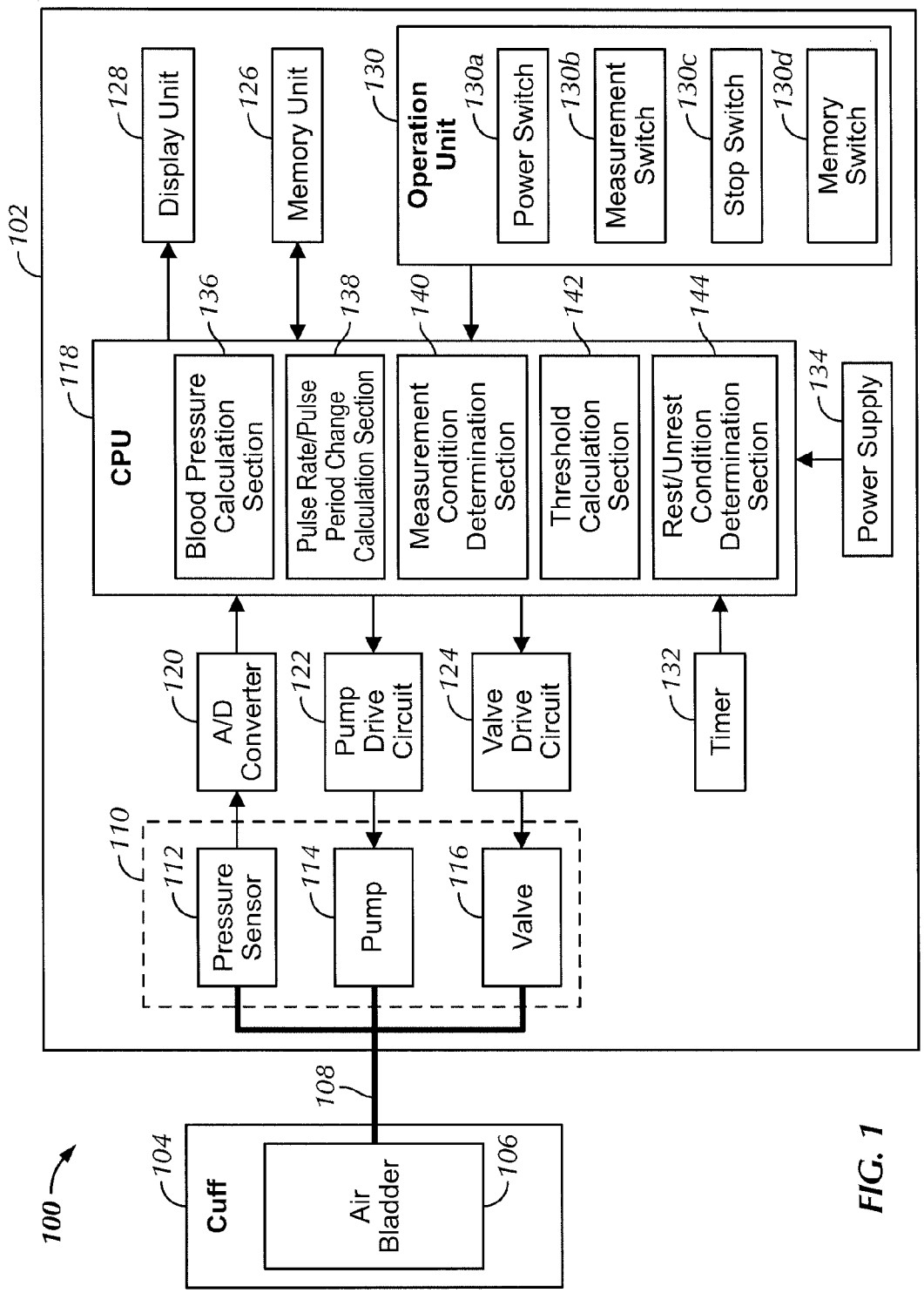
FIG. 1 is a functional block diagram showing a configuration of a blood pressure measurement device (sphygmomanometer) according to one or more embodiments of the present invention.

Hereinafter, embodiments of a blood pressure measurement device according to one or more embodiments of the present invention will be described with reference to the drawings. In the following description, the same reference numerals are given to the same components and constituent elements. The names and functions thereof are also the same.

FIG. 1 is a functional block diagram showing a configuration of a blood pressure measurement device (sphygmomanometer) according to one or more embodiments of the present invention.

Referring to FIG. 1, the blood pressure measurement device (sphygmomanometer) 100 is provided with a device main body 102 and a cuff 104. When blood pressure measurement is performed by the sphygmomanometer 100, the cuff 104, which has a belt-like outer shape, is wrapped around a measurement site of the patient. The cuff 104 houses an air bladder 106 serving as a fluid bag for compressing the measurement site.

The cuff 104 and the device main body 102 are connected by an air tube 108 serving as a connecting tube. According to one or more embodiments of the present invention, the air tube 108 consists of a flexible tube. One end of the air tube 108 is connected to a measurement air system 110 that is provided in the device main body 102. The other end of the air tube 108 is connected to the air bladder 106 of the cuff 104.

The measurement air system 110 supplies air to or discharges air from the air bladder 106 contained in the cuff 104 via air tube 108. The measurement air system 110 includes a pressure sensor 112 that detects the pressure inside the air bladder 106, and a pump 114 and a valve 116 for expanding and contracting the air bladder 106. Supplying air to the air bladder 106 pressurizes the cuff 104, while discharging air from the air bladder 106 depressurizes the cuff 104. The blood pressure measurement device (sphygmomanometer) 100 also includes a central processing unit (CPU) 118, an A/D converter 120, a pump drive circuit 122, and a valve drive circuit 124. The CPU 118 controls the entirety of the blood pressure measurement device (sphygmomanometer) 100. The A/D converter 120, the pump drive circuit 122, and the valve drive circuit 124 are connected to the measurement air system 110.

The pressure sensor 112 detects the internal pressure of the air bladder 106 and inputs a detection signal to the A/D converter 120. The input detection signal is converted to a digital signal by the A/D converter 120, and input to the CPU 118. The CPU 118 executes predetermined processing based on the internal pressure of the air bladder 106 obtained from the pressure sensor 112 and outputs control signals to the pump drive circuit 122 and the valve drive circuit 124 in accordance with the result of the predetermined processing.

The device main body 102 of the blood pressure measurement device (sphygmomanometer) includes a memory unit 126, which stores programs executed by the CPU 118 and results of measurement. That is, the memory unit 126 is constituted by a storage medium. Memory unit 126 may be realized by a single storage medium or more than one storage media. Exemplary storage media include media for storing programs in a non-volatile manner such as CD-ROM (Compact Disc-Read Only Memory), DVD-ROM (Digital Versatile Disk-Read Only Memory), USB (Universal Serial Bus) memory, memory card FD (Flexible Disk), hard disk, magnetic tape, cassette tape, MO (Magnetic Optical Disc), MD (MiniDisc), IC (Integrated Circuit) card (excluding memory card), optical card, mask ROM, EPROM, and EEPROM (Electronically Erasable Programmable Read-Only Memory).

The device main body 102 of the blood pressure measurement device (sphygmomanometer) 100 also includes a display unit 128 and an operation unit 130. The display unit 128 displays the results of measuring blood pressure values, pulse rates, states of rest or unrest, etc. using numerical values, labels, indicia, graphs, and the like in a manner that allows visible confirmation. A liquid crystal panel or the like, for example, may be used as the display unit 128. According to one or more embodiments of the present invention, the operation unit 130 includes a power switch 130a, a measurement switch 130b, a stop switch 130c, and a memory switch 130d.

The device main body 102 of the blood pressure measurement device (sphygmomanometer) 100 also includes a timer 132 and a power supply 134. The timer 132 has a clock function, and the power supply 134 supplies power to the CPU 118. According to one or more embodiments of the present invention, the power supply 134 supplies power to the CPU 118 from an external power supply. According to other embodiments of the present invention, the power supply 134 may be a battery or similar element that supplies power to the CPU 118 without receiving power from an external power supply.

As previously described, the operation unit 130 includes the power switch 130a, the measurement switch 130b, the stop switch 130c, and the memory switch 130d according to one or more embodiments of the present invention. The power switch 130a receives input of an instruction for turning the power supply on or off. The measurement switch 130b receives a measurement start instruction. The stop switch 130c receives a measurement stop instruction. Finally, the memory switch 130d receives an instruction to read out information such as blood pressure recorded in memory unit 126.

The CPU 118 includes a blood pressure calculation section 136 that calculates blood pressure values (a systolic blood pressure value, a diastolic blood pressure value, and/or an average blood pressure value) based on the internal pressure of the air bladder 106 obtained from the pressure sensor 112. The CPU 118 outputs the blood pressure values calculated by the blood pressure calculation section 136 to the display unit 128 to display them as a result of measurement.

The CPU 118 also includes a pulse rate/pulse period change calculation section 138 that calculates the pulse rate and pulse period change of a patient based on a measured pulse period of the patient for a particular phase lasting for a period of time. According to one or more embodiments of the present invention, the measured pulse period may be based on a time period of a detected pulse waveform and/or a change of pulse period. According to one or more embodiments of the present invention, the pulse rate/pulse period change calculation section 138 calculates the pulse rate of the patient during a time period by dividing the length of the time period by the average time period of pulse waves that occurred during measurement. According to one or more embodiments of the present invention, the pulse rate/pulse period change calculation section 138 calculates the pulse period change of the patient during a time period based on the difference between the maximum time period of a pulse and the minimum time period of a pulse that occurred during the measurement. The CPU 118 outputs the pulse rate calculated by the pulse rate/pulse period change calculation section 138 to the display unit 128 to display it as a result of measurement.

The CPU 118 also includes a measurement condition determination section 140 that determines which of a plurality of measurement conditions applies during blood pressure measurement. According to one or more embodiments of the present invention, the plurality of measurement conditions may include the time zone (time of day), day of the week, season, or environmental temperature.

The CPU 118 also includes a threshold calculation section 142 that calculates a threshold range for the pulse rate and pulse period change calculated by the pulse rate/pulse period change calculation section 138, with respect to each of the plurality of measurement conditions (i.e., each of the plurality of phases) determined by the measurement condition determination section 140. The CPU 118 outputs the threshold ranges calculated by the threshold calculation section 142 to the memory unit 126 for storage.

The CPU 144 also includes a rest/unrest condition determination section 144 that determines whether the patient is in a rest condition or an unrest condition during blood pressure measurement by comparing present pulse rate and/or pulse period change measurements with the threshold range of past pulse rate and/or pulse period change measurements. If it is determined that the present pulse rate and/or pulse period changes are outside (that is, above or below) the threshold range of past pulse rate and/or pulse period change measurements, then the rest/unrest condition determination section 144 determines that the patient was in an unrest condition during blood pressure measurement. On the other hand, if it is determined that the present pulse rate and/or pulse period changes are within the threshold range of past pulse rate and/or pulse period change measurements, then the rest/unrest condition determination section 144 determines that the patient was in a rest condition during blood pressure measurement. The CPU 118 outputs the determination of whether the patient was in an unrest or a rest condition during blood pressure measurement as determined by the rest/unrest condition determination section 144 to the display unit 128 to display it as a result of measurement.

Displaying the blood pressure measurement of the patient on the display unit 128 together with the determination of whether the patient was in an unrest or a rest condition during the blood pressure measurement allows the patient to decide whether the measured blood pressure is reliable.

Figure 2:
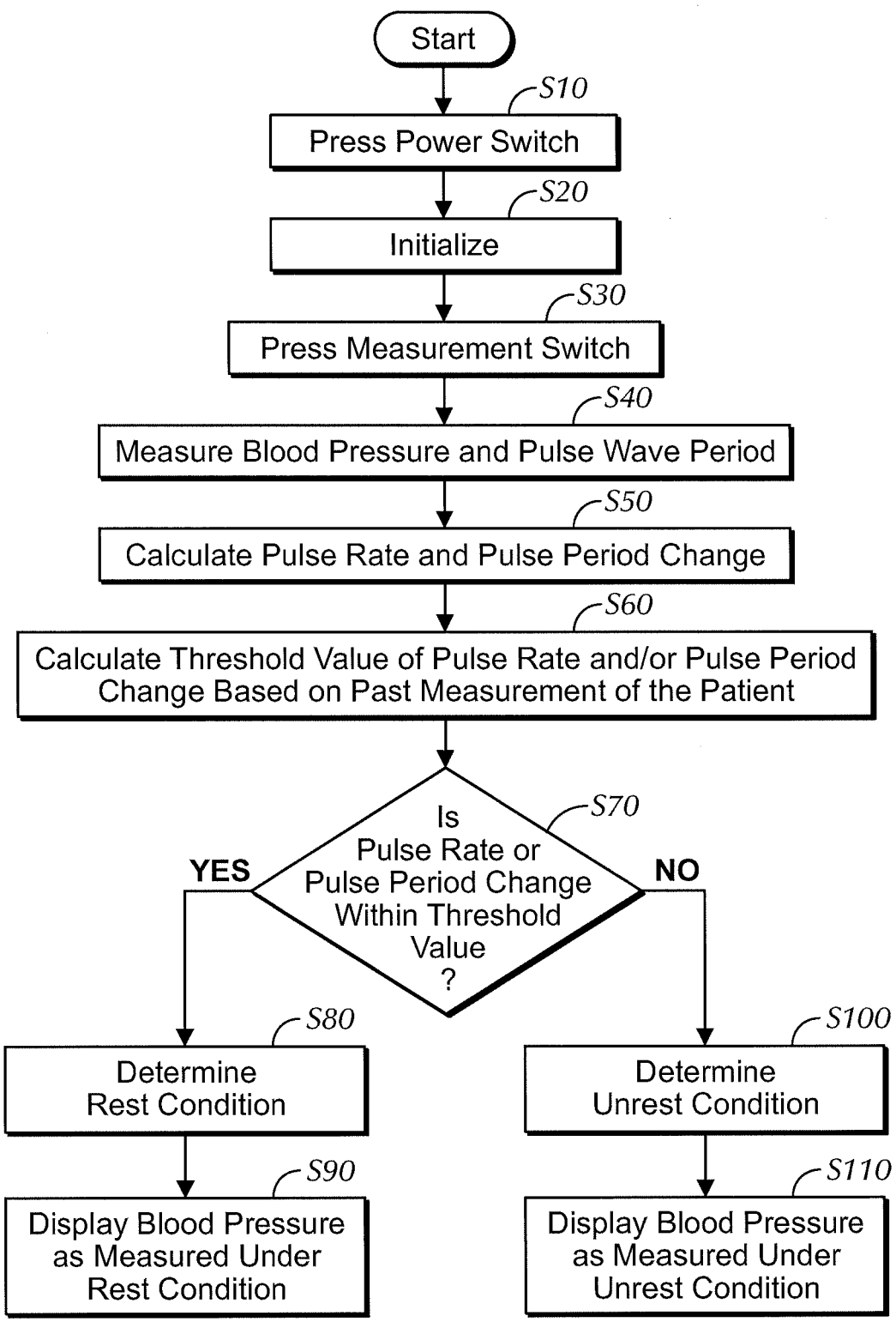
FIG. 2 is a flow chart of processing related to the determination of whether a patient was in a rest condition or an unrest condition during blood pressure measurement according to one or more embodiments of the present invention.

FIG. 2 is a flow chart of processing related to the determination of whether a patient was in a rest condition or an unrest condition during blood pressure measurement according to one or more embodiments of the present invention. In the blood pressure measurement device (sphygmomanometer) 100, this processing is realized by the CPU 118 executing a program stored in the memory unit 126 (or in a recording medium detachable from the device main body 102).

Referring to FIG. 2, in the blood pressure measurement processing, first at step S10, the CPU 118 stands by until the power switch 130a is operated, and advances the processing to step S20 when it is judged that the power switch 130a has been operated.

At step S20, the CPU 118 initializes the blood pressure measurement device (sphygmomanometer) 100. The internal pressure of the air bladder 106 of the cuff 104 is thereby initialized.

At step S30, the CPU 118 stands by until the measurement switch 130b is operated. When it is judged that the measurement switch 130b has been operated, the CPU 118 advances the processing to step S40.

At step S40, the CPU 118 performs the processing to measure the blood pressure (e.g., a systolic blood pressure value, a diastolic blood pressure value, and/or an average blood pressure value) and the pulse wave period of the patient. The CPU 118 then advances the processing to step S50.

At step S50, the CPU 118 performs the processing to calculate a "pulse rate" and a "pulse period change" of the patient based on the data obtained during measurement of the blood pressure and the pulse wave period during step S40. According to one or more embodiments of the present invention, the CPU 118 calculates the pulse rate of the patient by dividing the length of the time period by the average time period of pulse waves that occurred during the measurement. According to one or more embodiments of the present invention, the CPU 118 calculates the pulse period change of the patient for a particular time period based on a difference between a maximum pulse period and a minimum pulse period that occurred during the measurement. After calculating the pulse rate and the pulse period change of the patient, the CPU 118 then advances the processing to S60.

At step S60, the CPU 118 performs the processing to calculate a threshold value of the pulse rate and/or the pulse period change of the patient. According to one or more embodiments of the present invention, the pulse wave period may be measured a plurality of times at step S40, and at step S50, an average of a plurality of pulse rates and pulse period changes may be calculated so that, at step S60, an average of the plurality of pulse rates and pulse period changes may be used to calculate the threshold value ranges. Using an average of the plurality of the pulse rates and pulse period changes in accordance with one or more embodiments of the present invention may result in more reliable threshold value ranges.

According to one or more embodiments of the present invention, the upper end threshold value and the lower end threshold value for the average value of the pulse rate or the pulse period change threshold range may be calculated using Equation 1 and Equation 2, as shown below.

Upper end of threshold value=Average value of pulse
  rate or pulse period change×(1+α)   Equation 1.

Lower end of threshold value=Average value of pulse
  rate or pulse period change×(1−α)   Equation 2.

Figure 4:
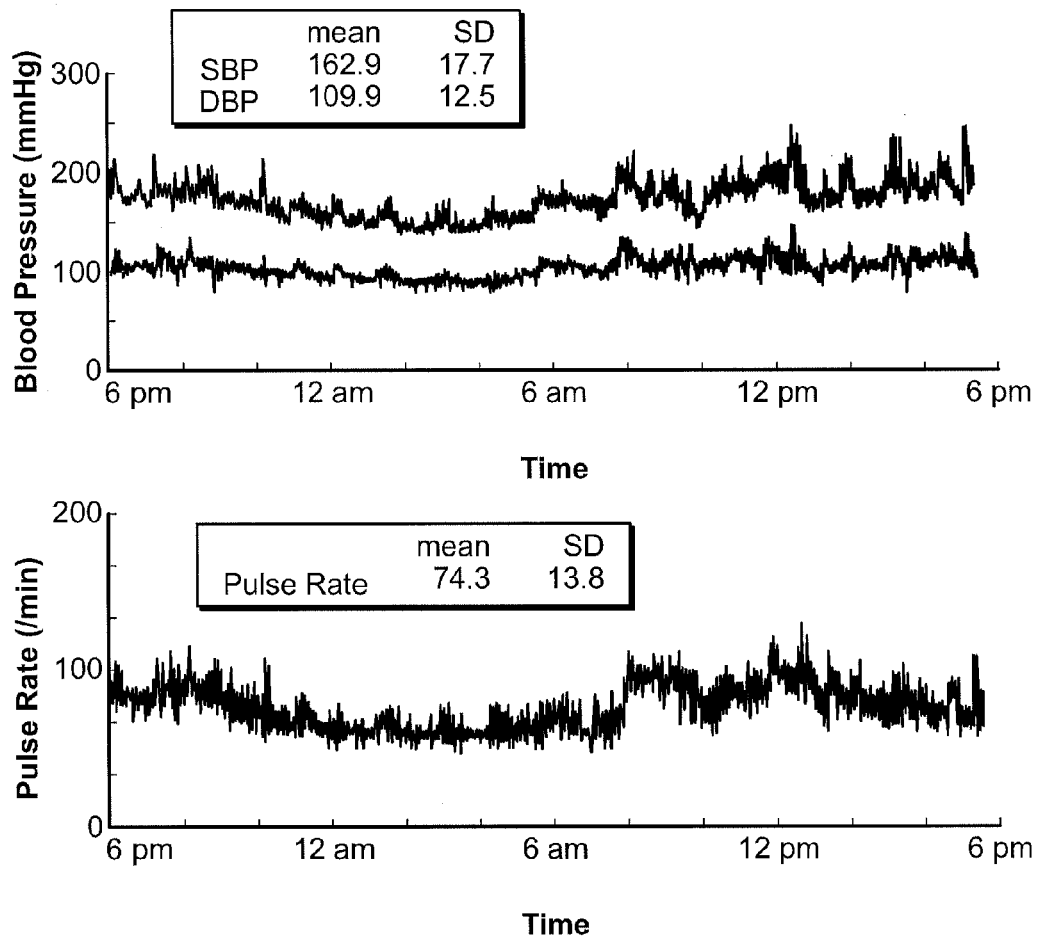
FIG. 4 shows an example of how blood pressure and pulse rate fluctuate depending on the time zone of measurement.

As shown, "α" of Equation 1 and Equation 2 may be set discretionarily to account for the tendency of the blood pressure value and the pulse rate of the patient. Referring now to FIG. 4, an example of how blood pressure and pulse rate fluctuate depending on the time zone of measurement is shown for a particular patient. As shown in FIG. 4, the patient's fluctuation of pulse rate tends be larger during the daytime zone, as compared with the nighttime zone. Therefore, if the blood pressure measurement was conducted during the daytime time zone, α of Equation 1 and Equation 2 may be set to be 0.15. If the blood pressure measurement was conducted during the nighttime zone, α of Equation 1 and Equation 2 may be set to be 0.10.

After the CPU 118 performs the processing to calculate the pulse rate and/or pulse period change threshold value ranges, the CPU 118 advances the processing to step S70 to determine whether the measured pulse rate or pulse period change is within or beyond the calculated threshold value range. If the measured pulse rate or pulse period change is within the threshold value range, then the CPU 118 advances the processing to step S80 and determines that the patient was in a rest condition during blood pressure measurement. After step S80, the CPU 118 advances the processing to step S90 to display on the display unit 128 the determination that the patient was in a rest condition during blood pressure measurement. On the other hand, if the measured pulse rate or pulse period change is beyond the threshold value range, then the CPU 118 advances the processing to step S100 and determines that the patient was in an unrest condition during blood pressure measurement. After step S100, the CPU advances the processing to step S110 to display on the display unit 129 the determination that the patient was in an unrest condition during blood pressure measurement.

FIGS. 3A and 3B are examples of data tables that show the blood pressure measurements, pulse rates, pulse period changes, and time zones (times of day) of Patient A and Patient B according to one or more embodiments of the present invention. As shown in FIG. 3A, the pulse rate and the pulse period change of Patient A was measured together with the time zone (time of day) in which the measurement was conducted. According to one or more embodiments of the present invention, the time periods for the daytime and nighttime time zones may be set as follows:
Daytime=8:00 AM-10:00 PM.
Nighttime=10:00 PM-8:00 AM.

As previously described, according to one or more embodiments of the present invention, the CPU 118 calculates the pulse rate of the patient by dividing the length of the time period by the average time period of pulse waves (that is, the average pulse period) that occurred during the measurement. Moreover, according to one or more embodiments of the present invention, the CPU 118 calculates the pulse period change of the patient for a particular time period based on a difference between a maximum pulse period and a minimum pulse period that occurred during the measurement. Accordingly, the pulse rate and the pulse period change of a patient may be calculated using Equation 3 and Equation 4 as follows:

Pulse rate=60 sec÷(average time period (sec) of pulse
  waves in a measurement)   Equation 3.

Pulse period change=maximum time period of a pulse
  wave in a measurement−minimum time period of
  a pulse wave in a measurement   Equation 4.

The results of the calculations of the pulse rate and the pulse period change of Patient A using Equation 3 and Equation 4, according to one or more embodiments of the present invention, are shown in FIG. 3(A).

According to one or more embodiments of the present invention, the upper end of the pulse rate threshold value range and the lower end of the pulse rate threshold value range for Patient A may be calculated based on Equation 1 and Equation 2, as previously described, as shown below.

Upper end of pulse rate threshold value
  range=Average value of pulse rate×(1+α)

Lower end of pulse rate threshold value
  range=Average value of pulse rate×(1−α)

As previously described, "a" may be set discretionarily to account for the tendency of the blood pressure value and the pulse rate of the patient. Therefore, if the blood pressure measurement was conducted during the daytime time zone, α may be set to be 0.15. If the blood pressure measurement was conducted during the nighttime zone, α may be set to be 0.10.

Still referring to FIG. 3(A), with respect to the average of the pulse rate measurements of 1)-3) for Patient A, which pulse rate measurements were all conducted during the daytime time zone, the upper end of the pulse rate threshold value range is 81×(1+0.15)=93.15, and the lower end of the pulse rate threshold value range is 81×(1−0.15)=68.85.

As further shown in FIG. 3(A), for measurement 4), the pulse rate of Patient A was measured to be 101, which is beyond the upper end of the pulse rate threshold value range of 93.15. Therefore, it is determined that measurement 4) was conducted when Patient A was in an unrest condition.

According to one or more embodiments of the present invention, the upper end of the pulse period change threshold value range and the lower end of the pulse period change threshold value range of Patient A may be calculated based on Equation 1 and Equation 2, as previously described, as shown below.

Upper end of pulse period change threshold
  value=Average value of pulse period change×(1+
  α)

Lower end of pulse period change threshold
  value=Average value of pulse period change×(1−
  α)

As previously described, "α" may be set discretionarily to account for the tendency of the blood pressure value and the pulse rate of the patient. Therefore, if the blood pressure measurement was conducted during the daytime time zone, α may be set to be 0.15. If the blood pressure measurement was conducted during the nighttime zone, α may be set to be 0.10.

Still referring to FIG. 3(A) with respect to the pulse period change measurements of 1)-3) for Patient A, which pulse period change measurements were all conducted during the daytime time zone, the upper end of the pulse period change threshold value range is 0.033×(1+0.15)=0.03795, and the lower end of the pulse rate threshold value range is 0.033×(1−0.15)=0.02805.

As further shown in FIG. 3(A), for measurement 4), the pulse period change for Patient A was measured to be 0.104, which is beyond the upper end of the pulse period change threshold value range of 0.03795. Therefore, it is determined that measurement 4) was conducted when Patient A was in the unrest condition.

Referring now to FIG. 3(B), the pulse rate and the pulse period change of Patient B was measured together with the time zone (time of day) in which the measurement was conducted. According to one or more embodiments of the present invention, the time periods for the daytime and nighttime time zones may be set as follows.
Daytime=8:00 AM-10:00 PM.
Nighttime=10:00 PM-8:00 AM.

The results of the calculations of the pulse rate and the pulse period change of Patient B using Equation 3 and Equation 4, according to one or more embodiments of the present invention, are shown in FIG. 3(B).

According to one or more embodiments of the present invention, the upper end of the pulse rate threshold value range and the lower end of the pulse rate threshold value range of Patient B may be calculated based on Equation 1 and Equation 2, as previously described, as shown below.

Upper end of pulse rate threshold value range=Average value of pulse rate×(1+α)

Lower end of pulse rate threshold value range=Average value of pulse rate×(1−α)

As previously described, "α" may be set discretionarily to account for the tendency of the blood pressure value and the pulse rate of the patient. Therefore, if the blood pressure measurement was conducted during the daytime time zone, α may be set to be 0.15. If the blood pressure measurement was conducted during the nighttime zone, α may be set to be 0.10.

As shown in FIG. 3(B), measurement 8) was conducted during the daytime zone. As such, only measurements 5) and 6), which were also conducted during the daytime time zone, should be used to calculate the pulse rate threshold value range for Patient B. Therefore, with respect to the average of the pulse rate measurements of 5)-6) for Patient B, the upper end of the pulse rate threshold value range is 88×(1+0.15) =101.2, and the lower end of the pulse rate threshold value range is 88×(1−0.15)=74.8.

As further shown in FIG. 3(B), for measurement 8), which was conducted during the daytime, the pulse rate of Patient B was measured to be 98, which is within the pulse rate threshold value range of 74.8 to 101.2. Therefore, it is determined that measurement 8) was conducted when the patient was in a rest condition.

FIGS. 5(A) and 5(B) are example displays of the data shown in FIGS. 3(A) and 3(B) according to one or more embodiments of the present invention. Specifically, FIG. 5(A) shows an example display of measurement 4) of Patient A as shown in FIG. 3. FIG. 5(B) shows an example display of measurement 8) of Patient B as shown in FIG. 3.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. A blood pressure measurement device that determines whether a patient was in a rest condition or an unrest condition during blood pressure measurement, the device comprising:
    means for measuring a pulse period of the patient;
    a memory that stores data of the measured pulse period and data of a pulse period of a past measurement of the patient;
    a threshold calculation section that calculates a threshold value range based on the data of the pulse period of the past measurement of the patient individually with respect to each patient,
        wherein an upper end of the threshold value range is a product of an average value of the data of the pulse period of the past measurement of the patient, and one plus a discretionary value that accounts for a tendency of a blood pressure value and a pulse rate of the patient;
    a rest/unrest condition determination section that determines whether the patient was in the rest condition or the unrest condition during blood pressure measurement by comparing the data of the measured pulse period with the threshold value range based on the data of the pulse period of the past measurement of the patient; and
    a display unit that displays the blood pressure measured and whether the blood pressure was measured when the patient was in the rest condition or the unrest condition.

2. The blood pressure measurement device according to claim 1, wherein the data of the measured pulse period and the data of the pulse period of past measurement of the patient each comprise a pulse rate and a pulse period change.

3. The blood pressure measurement device according to claim 1, wherein the threshold calculation section adjusts the threshold value range depending on a measurement condition of the measurement.

4. The blood pressure measurement device according to claim 1, wherein the rest/unrest condition determination section determines whether the patient was in the rest condition or the unrest condition during blood pressure measurement by examining both a pulse rate and a pulse period change of the patient, and if at least one of the pulse rate and the pulse period change is found to be different from a pulse rate and a pulse period change of past measurement by more than a corresponding threshold value, the patient is determined to have been in the unrest condition during blood pressure measurement, wherein the pulse rate and the pulse period change of the patient are based on the pulse period of the patient.

5. A blood pressure measurement device that determines whether a patient was in a rest condition or an unrest condition during blood pressure measurement, the device comprising:
    a cuff having an air bladder, wherein the cuff is configured to be wrapped around a measurement site of the patient;
    a measurement air system comprising a pressure sensor, a pump, and a valve;
    an air tube that connects the air bladder of the cuff to the measurement air system;
    a blood pressure calculation section that calculates a blood pressure of the patient based on an internal pressure of the air bladder as detected by the pressure sensor;
    a pulse rate/pulse period change calculation section that calculates a pulse rate and a pulse period change of the patient based on a measured pulse period of the patient;
    a memory that stores the pulse rate and the pulse period change of the patient and data of a pulse period of a past measurement of the patient;
    a threshold calculation section that calculates a threshold value range based on the data of the pulse period of the past measurement of the patient individually with respect to each patient,
        wherein an upper end of the threshold value range is a product of an average value of the data of the pulse period of the past measurement of the patient, and one plus a discretionary value that accounts for a tendency of a blood pressure value and a pulse rate of the patient;

a rest/unrest condition determination section that determines whether the patient was in the rest condition or the unrest condition during blood pressure measurement by comparing the pulse rate or the pulse period change of the patient with the threshold value range based on the data of the pulse period of the past measurement of the patient; and a display unit that displays the blood pressure measured and whether the blood pressure was measured when the patient was in the rest condition or the unrest condition.

6. The blood pressure measurement device according to claim 5, wherein the data of the pulse period of the past measurement of the patient comprise a past measurement pulse rate and a past measurement pulse period change.

7. The blood pressure measurement device according to claim 5, wherein the threshold calculation section adjusts the threshold value range depending on a measurement condition of the measurement.

8. The blood pressure measurement device according to claim 5, wherein the rest/unrest condition determination section determines whether the patient was in the rest condition or the unrest condition during blood pressure measurement by examining both the pulse rate and the pulse period change of the patient, and if at least one of the pulse rate and the pulse period change is found to be different from a pulse rate and a pulse period change of past measurement by more than a corresponding threshold value, the patient is determined to have been in the unrest condition during blood pressure measurement.

9. A method of determining whether a patient was in a rest condition or an unrest condition during blood pressure measurement, the method comprising:

measuring, by a sphygmomanometer, a blood pressure, a pulse rate, and a pulse period change of the patient;

storing data of the pulse rate and the pulse period change obtained by the measurement in a memory;

calculating, by a threshold calculation section, a first threshold value range based on data of a pulse rate of a past measurement of the patient individually with respect to each patient, wherein an upper end of the first threshold value range is a product of an average value of the data of the pulse rate of the past measurement of the patient, and one plus a discretionary value that accounts for a tendency of the blood pressure and the pulse rate of the patient;

calculating, by the threshold calculation section, a second threshold value range based on data of a pulse period change of a past measurement of the patient individually with respect to each patient, wherein an upper end of the second threshold value range is a product of an average value of the data of the pulse period change of the past measurement of the patient, and one plus the discretionary value that accounts for the tendency of the blood pressure and the pulse rate of the patient;

determining, by a rest/unrest condition determining section, whether the patient was in the rest condition or the unrest condition during blood pressure measurement by comparing the measured pulse rate and the measured pulse period change with the first threshold value range and the second threshold value range, respectively, based on data of the pulse rate and the pulse period change of the past measurement of the patient; and displaying on a display unit the blood pressure measured and whether the blood pressure was measured when the patient was in the rest condition or the unrest condition.

10. The method according to claim 9, further comprising adjusting at least one of the first threshold value range and the second threshold value range depending on a condition of the measurement.

11. The method according to claim 9, further comprising determining whether the patient was in the rest condition or the unrest condition during blood pressure measurement by examining both the measured pulse rate and the measured pulse period change, and if at least one of the measured pulse rate and the measured pulse period change is found to be outside the first threshold value range and the second threshold value range, respectively, based on the data of the pulse rate and the pulse period change of the past measurement of the patient, determining that the patient was in the unrest condition during blood pressure measurement.

* * * * *